United States Patent [19]
Nuss

[11] Patent Number: 5,710,430
[45] Date of Patent: *Jan. 20, 1998

[54] METHOD AND APPARATUS FOR TERAHERTZ IMAGING

[75] Inventor: Martin C. Nuss, Fair Haven, N.J.

[73] Assignee: Lucent Technologies Inc., Murray Hill, N.J.

[*] Notice: The term of this patent shall not extend beyond the expiration date of Pat. No. 5,623,145.

[21] Appl. No.: 711,823

[22] Filed: Sep. 10, 1996

Related U.S. Application Data

[62] Division of Ser. No. 388,933, Feb. 15, 1995, Pat. No. 5,623,145.

[51] Int. Cl.⁶ .......................... G01N 21/17; G01N 21/49
[52] U.S. Cl. .................. 250/358.1; 250/330; 250/341.1
[58] Field of Search ........................ 250/341.1, 358.1, 250/359.1, 330

[56] References Cited

U.S. PATENT DOCUMENTS

| | | | |
|---|---|---|---|
| 5,148,022 | 9/1992 | Kawaguchi et al. | 250/341.1 X |
| 5,371,368 | 12/1994 | Alfano et al. | 250/358.1 X |
| 5,441,054 | 8/1995 | Tsuchiya | 250/341.1 X |
| 5,477,051 | 12/1995 | Tsuchiya | 250/341.1 |
| 5,623,145 | 4/1997 | Nuss | 250/330 |

*Primary Examiner*—Edward J. Glick
*Attorney, Agent, or Firm*—Steven R. Bartholomew; Brian K. Dinicola

[57] ABSTRACT

Certain material and objects can be characterized by a frequency-dependent absorption, dispersion, and reflection of terahertz transients in signals which pass illuminate the material or object. The present terahertz imaging system analyses that frequency dependence in the time-domain by collecting that transmitted signal propagating through the object and then processing the information contained in those signals for every point or "pixel" on that object. This is a non-invasive imaging technique that is capable of differentiating between different materials, chemical compositions, or environments.

12 Claims, 4 Drawing Sheets

METHOD AND APPARATUS FOR TERAHERTZ IMAGING

This application is a divisional of parent application Ser. No. 08/388,933 filed Feb. 15, 1995 and entitled, "Method and Apparatus of Terahertz Imaging", now U.S. Pat. No. 5,623,145.

TECHNICAL FIELD

This invention relates to spectroscopy in the terahertz frequency range and, more particularly, to a method and apparatus for creating images of objects with signals in this frequency range.

BACKGROUND OF THE INVENTION

Terahertz time-domain spectroscopy ("THz-TDS") is a very powerful spectroscopic technique in the far-infrared spectral region. Terahertz radiation has been generated and detected using optically gated transmitters and receivers such as photoconducting dipole antennae as described in P. Smith et al., *IEEE J. of Quantum Electronics*, Vol. 24, No. 2, pp. 255–260 (1988) and N. Katzenellenbogen et al., *Appl. Phys. Lett.*, Vol. 58, No. 3, pp. 222–224 (1991). With these techniques, terahertz spectroscopy offers a reasonably good signal-to-noise ratio (up to approximately $10^4$); it can be performed without special thermal stabilization apparatus such as cooled detectors; it can be realized in a compact system; and it offers a transmitter and detector technology which is compatible with integrated circuit technology.

Numerous experiments using terahertz time domain spectroscopy have been performed on solids, liquids, and gases. Some experiments have analyzed the spectrum of a terahertz signal affected by carriers in semiconductors and superconductors. Other experiments have performed terahertz time domain spectroscopy on water vapor as well as $N_2O$ gas. Still other experiments have reported terahertz time domain spectroscopy of chemical compounds in the liquid phase. In all these experiments, the terahertz signal was transmitted through the object under study in a single illuminated volume region (usually 25 mm in diameter) to provide the spectral information about that homogeneous region.

SUMMARY OF THE INVENTION

Time domain spectroscopy and, more particularly, terahertz signals can be used for imaging objects by collecting individual signals propagating through distinct (spatially separate) points on the object and processing these signals to create the image of the object. It is also possible to focus the signal source on the object at distinct points and scan the source and detector in synchronism across the object in a pattern transverse to the propagation direction. Additionally, it is possible to cause the source to bathe the entire object with substantially parallel beams which could then be sampled by a detector scanning the object. Of course, in an alternative embodiment it would be possible to translate the object in the appropriate transverse directions while holding the focused transmitter and receiver in substantially fixed positions.

BRIEF DESCRIPTION OF THE DRAWING

A more complete understanding of the invention may be obtained by reading the following description of specific illustrative embodiments of the invention in conjunction with the appended drawing in which.

DETAILED DESCRIPTION

Figure 1:
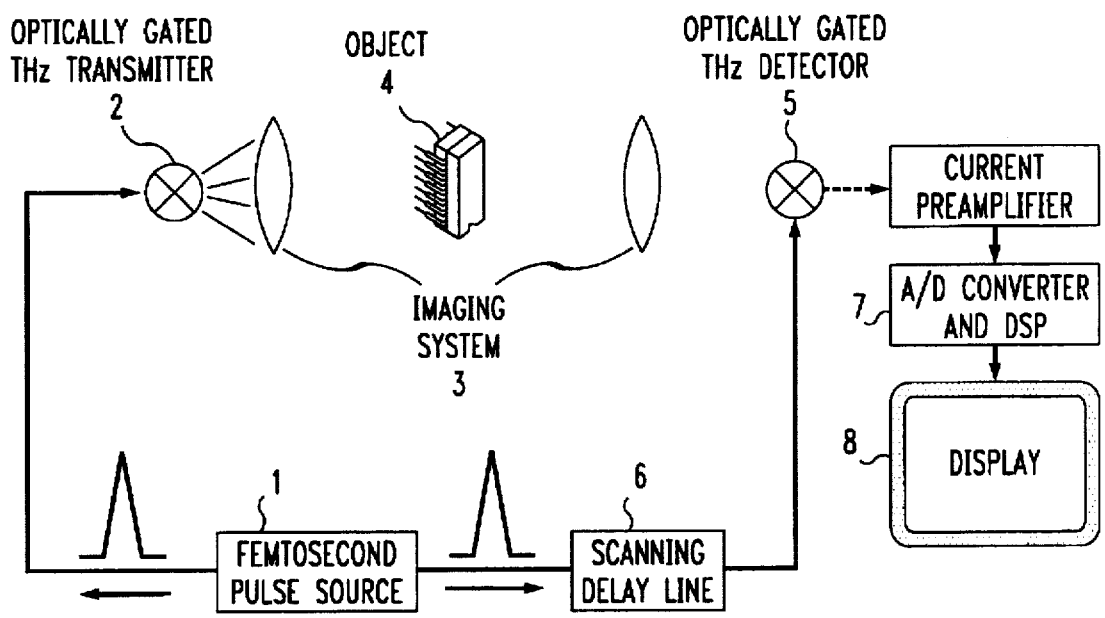
FIG. 1 shows a simplified block diagram of an illustrative terahertz imaging system in accordance with the principles of the present invention.

The THz imaging system of FIG. 1 in accordance with the present invention includes a source 1 of repetitive, femtosecond duration, optical pulses, an optically gated transmitter 2 of THz transients having a broad spectral bandwidth, imaging optics 3 comprising lenses and/or mirrors, an object 4 to be investigated, a time-gated detector or detector array 5, a scanning delay 6 capable of changing the delay between the femtosecond gating pulses on the transmitter and detector(s) at a rate of a few Hz to hundreds of Hz for the purpose of temporally heterodyning the THz-frequency transients down into the acoustic (Hz) range so that they can be processed by electronic techniques, a digital signal processing unit 7 including a digital signal processor and an A/D converter to process the time-domain data and extract the desired information, and a display 8 to view the image.

Certain material and objects can be characterized by a frequency-dependent absorption, dispersion, and reflection of terahertz transients in signals which pass through the material or object. The present terahertz imaging system analyses that frequency dependence in the time-domain by collecting that transmitted signal propagating through the object and then processing the information contained in those signals for every point or "pixel" on that object. This is a non-invasive imaging technique that is capable of differentiating between different materials, chemical compositions, or environments. This technique has applications not solely limited to biomedical imaging of tissue, "safe X-rays", chemical reaction analysis, environmental and pollution control, process control, materials inspection, fault detection, non-contact mapping of the doping in semiconductor wafers, profiling of doping and defects in laser crystals, and packaging inspection.

A typical terahertz transmitter emits a single cycle of electromagnetic radiation centered at 1 THz after being illuminated by a 100 fs laser pulse from either a modelocked dye laser operating around 620 nm or a modelocked Ti:Sapphire or Cr:LiSAF laser operating around 800 nm. Because of the short duration of the THz-transient, the spectrum is broadband, typically extending from less than 100 GHz to several THz.

No electronic circuit is capable of measuring and processing THz bandwidth electrical signals directly at this time. Sampling techniques based on the repetitive nature (typically ≈100 MHz repetition rate) of the optical and THz pulses can be used to measure the THz waveforms provided that the sampling window is shorter than any THz transient to be measured. Typical photoconducting sampling gates have sampling times shorter than 0.5 ps and are thus able to measure frequency transients in excess of 2 THz. No fast electronics is needed in the sampling technique, and only the average photocurrent in the dipole antenna is measured. Similar to a sampling scope, the delay between the THz waveform and the detector gating pulse is scanned slowly at a rate of about 10–100 Hz. Thus, each sampling pulse samples the THz pulse at a somewhat different time, until the entire THz waveform has been reconstructed from the samples. This leads to a "temporal down conversion" of the THz waveform into the kHz range, where it can readily be processed by electronics. This sampling technique is also known as Equivalent-Time-Sampling but is otherwise used in any commercial digital sampling oscilloscope. This isochronous sampling technique has been described for picosecond optical sampling by K. Weingarten et al. in *IEEE J. of Quantum Electronics*, Vol. 24, No. 2, pp. 198–220 (1988).

Many, if not most, compounds show very strong frequency-dependent absorption or reflection within the frequency range covered by these THz transients. Also, molecules and chemical compounds, at least in the gas phase, but also ions in certain crystals, have strong and sharp absorption lines in the THz spectral regions. The absorption lines are characteristic of the material under study such as a water molecule and its environment and can serve as a "fingerprint" of the molecule. Each chemical substance hence leads to a characteristic THz waveform that identifies the chemical composition and environment of the sample. There are also materials that are completely opaque to THz radiation such as metals and other materials with high electrical conductivity.

Figure 2:
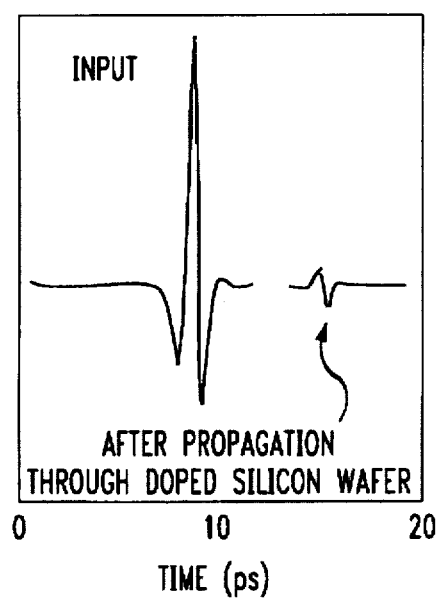
FIGS. 2 and 3 show comparisons between input terahertz waveforms and the output waveform after propagating through a known material.
Figure 3:
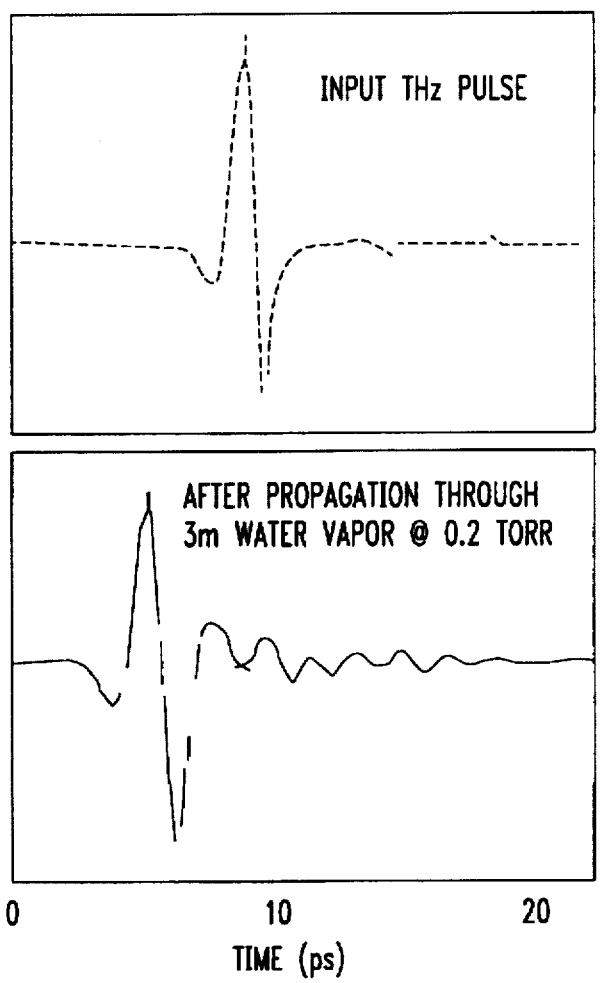

In the present THz imaging system, the spectra described above need not be computed or directly measured. Instead, the relevant information can be extracted right from the time-domain data, in a manner similiar to speech recognition and processing. In FIGS. 2 and 3 are the input THz waveforms (dashed) and the waveforms after propagation through the doped silicon sample (FIG. 2) and water vapor (FIG. 3).

The digital signal processor can recognize the characteristic shapes of the transmitted THz waveforms (specific shape change and attenuation in one case for silicon and ringing with characteristic frequency in the other case for water vapor), to determine the particular material at the spot illuminated by the THz beam. This requires training (or loading) the DSP with these specific waveforms in advance. Such a procedure is well within the knowledge of persons skilled in the art and will not be repeated here.

Figure 4:
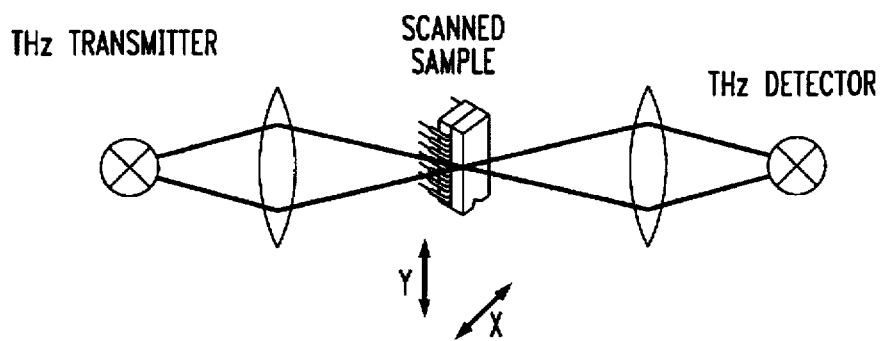
FIGS. 4 through 6 show illustrative embodiments for insuring a desired amount of scanning for the object to be scanned by the system of FIG. 1.

In a particular embodiment shown in FIG. 4 for the transmitter, receiver, and optics of FIG. 1, the THz beam emerging from the transmitter is focused to a diffraction-limited spot of 0.3–0.5 mm diameter. This is the diffraction-limited spot size for 1 THz radiation and close to the best spatial resolution possible with this technique. This spot is then imaged onto a single THz detector. The sample is placed in the focal plane of the THz beam and scanned in x and y in a zigzag pattern using two orthogonal, motor driven translation stages (shown pictorially by the x and y arrows).

The delay between transmitter and detector gating pulses is continuously scanned by a 10 Hz scanning delay line. The amplitude of the scanning delay line can be adjusted and determines the time window of data acquisition—a 1 mm amplitude corresponds to a 6.7 ps time window. The average photocurrent induced in the photoconducting dipole detector is measured with a current-to-voltage converter and then fed to a A/D-converter and DSP processor card. We use an A/D-converter capable of a 50 kHz conversion rate, and a DSP processor that can Fourier-transform the waveforms at a rate of 100 FFTs each second. Thus, with this system we can easily obtain the FFT spectrum of each THz waveform synchronously with the 10 Hz scan rate.

In an example from practice, the FFT spectrum is represented on the display screen as a colored dot with the frequency components of the THz spectrum represented by the frequencies of the visible (rainbow) spectrum. That is, the terahertz spectrum is mapped onto the visible spectrum and only those frequency components which propagate through the object under study can contribute to the displayed color.

Since DSPs are used in this system, it is also possible to utilize time domain techniques by computing the convolution (correlation) between the received terahertz signals and stored patterns which are related to particular elements, compounds, etc. The signals which most closely match the received signals will identify the point of the object being scanned.

In another example from experimental practice, the DSP processor looks for certain absorption lines which are characteristic of a specific molecule and assigns a specific color and intensity to this absorption pattern. After each scan, the sample is moved by one "pixel" (preferably roughly the spot size of the THz beam on the sample) and the display is updated for that particular pixel. With the above system, a 50×50 image can be acquired and displayed in just over 4 minutes.

Figure 8:
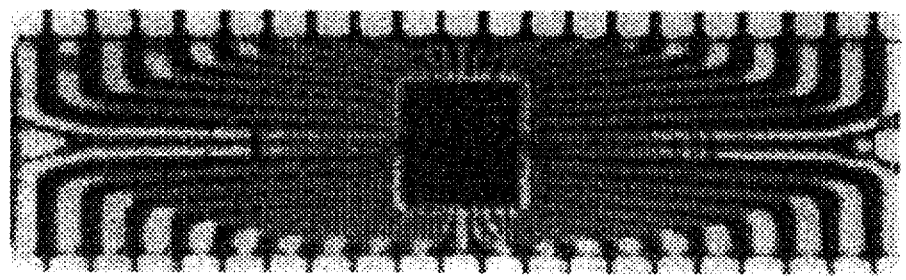
FIG. 8 shows an image of a semiconductor dual-in-line packaged chip produced by the illustrated terahertz imaging system.

FIG. 8 shows a preliminary result for a THz image obtained as described above. The picture is a so-called "THz X-Ray" of a packaged semiconductor chip.

Figure 5:
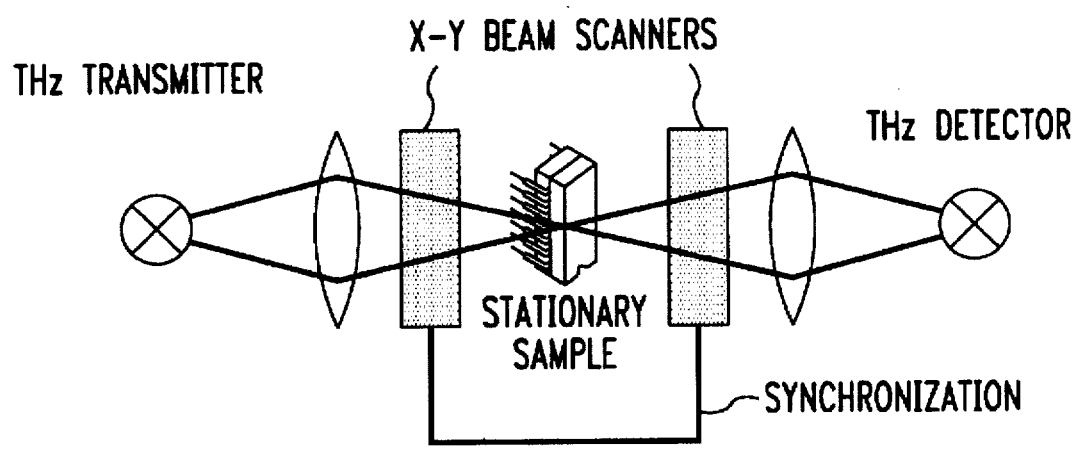

In another embodiment shown in FIG. 5 for the transmitter, receiver, and optics of the imaging system in FIG. 1, the sample remains stationary and the THz beams are scanned across the sample. This can be done either by mechanically steering the THz beam with mirrors or by optical steering of the THz beam (in which case, steering of the optical beams causes a steering of the THz beams).

Figure 6:
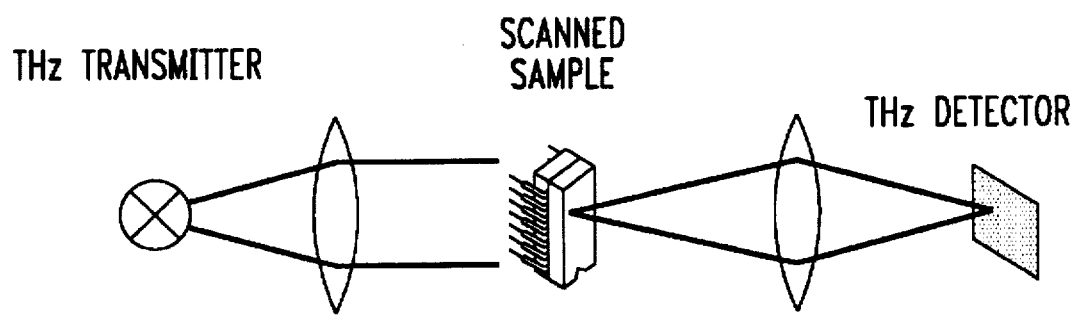
Figure 7:
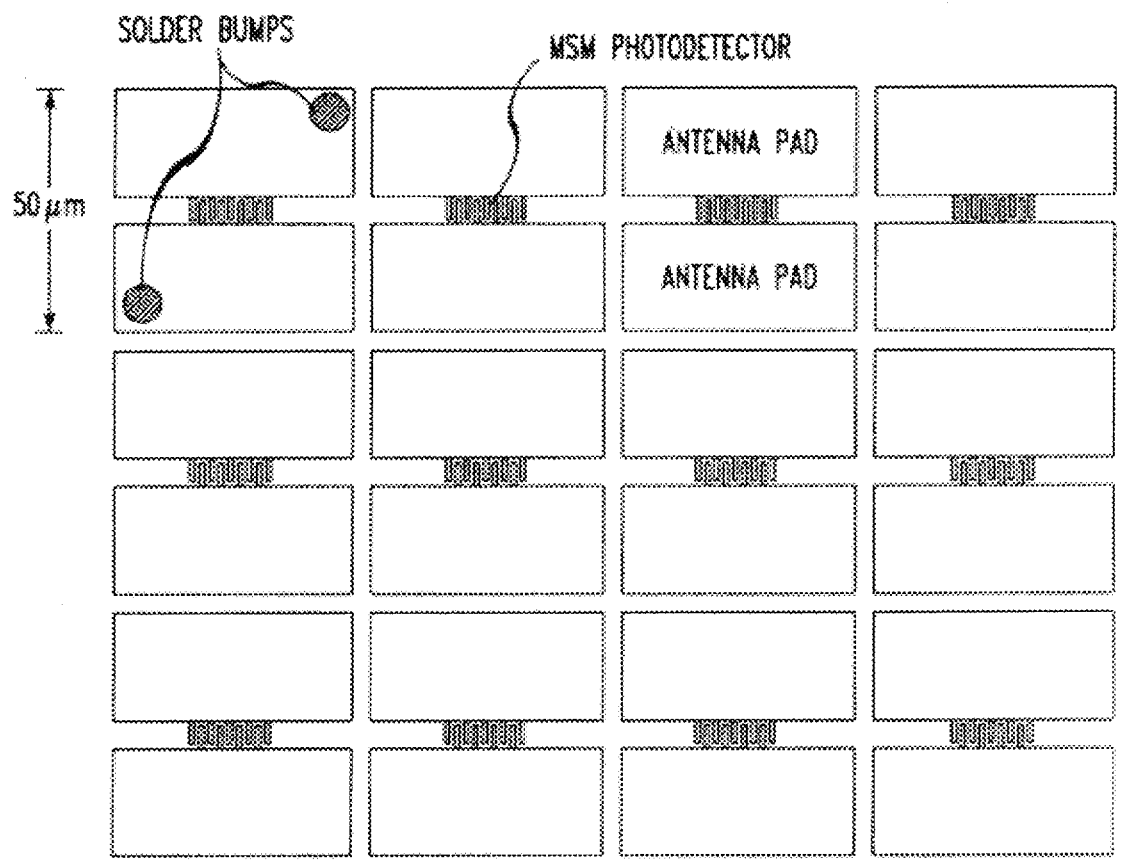
FIG. 7 shows a portion of an illustrative terahertz focal plane array useful in the embodiment in FIG. 6.

In the embodiment shown in FIG. 6 for the transmitter, receiver, and optics of the imaging system in FIG. 1, THz waveforms for the entire sample are acquired simultaneously by using a focal-plane THz detector array as shown in FIG. 7. Here, the entire sample is flood-illuminated by a THz beam, and the sample is imaged onto the focal-plane detector array using a lens system. The flood-illumination causes the illumination to appear as parallel beams from individual point sources.

The focal plane THz detector array consists of a two-dimensional array of THz dipole antennas (in this case 50 µm on each side) which are lithographically defined on a low temperature (LT)-GaAs or radiation-damaged Silicon-on-Sapphire (SOS) chip so that the gating time is subpicosecond. Monolithic semiconductor module (MSM) photoconductive switches using interdigitated finger contacts are defined between the antenna chip. The size of the interdigitated photoconductive MSM switch is roughly 10 µm square. Each of the antenna/MSM photoconductive switches constitutes a THz image pixel. The MSM photoconductive switches are gated by a short optical pulse derived from a beam that covers the entire area of the chip and is focused onto the MSM photoconductive switches using a microlens array. The microlens array and the gate pulse can either come from the same side as the THz radiation (with a beam splitter), or from opposite sides (in this case the THz beam travels through the chip substrates before it is detected by the antennas). Only 1 pJ of readout energy is required for each MSM photoconductive switche, so that a 10 nJ optical pulse can gate a 100×100 focal plane array. The antenna chip is solder bump-bonded to another chip underneath with one contact on each antenna pad that carries the detected photocurrent off the chip and to the DSP processor. Preferably, the underlying chip contacted by the solder bumps is a charge-coupled device (CCD) array, so that all pixels can be read out sequentially like a video camera. The photogenerated charges are accumulated in the CCD array over many optical pulses before the charge is read out.

What is claimed is:

1. A method of inspecting a medium having one or more absorptive, dispersive, or reflective constituents, comprising the steps of:

directing a pulsed sequence of electromagnetic signals that are in the frequency range between 100 GHz to 20 THz at said medium, wherein the pulsed sequence is selected so as to permit observation of frequency dependent variations in the absorption, dispersion, or reflectivity of at least one constituent of the medium; and detecting the directed pulse signals following propagation through the medium, the detected pulse signals being characterized by temporal distortions related to said frequency dependent variations, to thereby obtain spectral information about said constituents in real time.

2. The method according to claim 1, further including a step of:

analyzing the temporal distortions in the time domain to obtain said spectral information.

3. The method according to claim 2, further including a step of:

creating an image of said medium based on spectral information obtained during said analyzing step.

4. The method according to claim 2, further including a step of:

identifying at least one constituent of the medium based on spectral information obtained during said analyzing step.

5. The method according to claim 4, wherein said identifying step includes comparing spectral information obtained during said analyzing step with stored spectral information associated with a plurality of compositions.

6. The method according to claim 1, wherein said directing step includes causing said electromagnetic signals to propagate along a plurality of spatially distinct paths through said medium.

7. The method according to claim 1, wherein said directing step includes causing said electromagnetic signals to propagate along a plurality of spatially distinct paths so as to be incident on a plurality of spatially distinct areas of the medium.

8. An apparatus for inspecting a medium having one or more absorptive, dispersive, or reflective constituents, comprising:

a transmitter for directing a pulsed sequence of electromagnetic signals that are in the frequency range between 100 GHz to 20 THz at said medium, wherein the pulsed sequence is selected so as to permit observation of frequency dependent variations in the absorption, dispersion, or reflectivity of at least one constituent of the medium; and a detector for detecting the pulsed sequence following propagation through the medium, the detected pulsed sequence being characterized by temporal distortions related to said frequency dependent variations in the absorption, dispersion, or reflectivity of at least one constituent of the medium, to thereby obtain spectral information about said constituents in real time.

9. The apparatus according to claim 8, further including means for causing said electromagnetic signals to propagate along a plurality of spatially distinct paths through said medium.

10. The apparatus according to claim 8, further including means for causing said electromagnetic signals to propagate along a plurality of spatially distinct paths so as to be incident on a plurality of spatially distinct areas of the medium.

11. The apparatus according to claim 10, further including analyzing means coupled to the detector for analyzing the temporal distortions to thereby obtain said spectral information.

12. The apparatus according to claim 11, further including means for storing spectral information relating to a plurality of compositions and wherein said analyzing means comprises means for comparing obtained spectral information with said stored spectral information to thereby identify a constituent of the medium.

* * * * *